United States Patent [19]

Kurono et al.

[11] Patent Number: 4,985,569

[45] Date of Patent: Jan. 15, 1991

[54] PYRROLIZINE DERIVATIVE AND ITS MANUFACTURE

[75] Inventors: Masayasu Kurono; Yasuaki Kondo; Ryoichi Unno; Yukiharu Matsumoto; Hiromoto Kimura; Mitsuru Oka; Kiichi Sawai, all of Aichi, Japan

[73] Assignee: Sanwa Kagaku Kenkyusho Co., Ltd., Higashi, Japan

[21] Appl. No.: 350,990

[22] Filed: May 12, 1989

[30] Foreign Application Priority Data

Jun. 7, 1988 [JP] Japan .................. 63-138405

[51] Int. Cl.$^5$ ............................................. C07D 487/04
[52] U.S. Cl. ................................................... 548/453
[58] Field of Search ......................................... 548/453

[56] References Cited

FOREIGN PATENT DOCUMENTS

| | | | |
|---|---|---|---|
| 0039903 | 11/1981 | European Pat. Off. | 548/453 |
| 0083694 | 5/1983 | Japan | 548/453 |
| 61-229893 | 10/1986 | Japan . | |
| 61-254587 | 11/1986 | Japan . | |
| 62-16487 | 1/1987 | Japan . | |

OTHER PUBLICATIONS

Miyano et al., "Abstract on the 97th Annual Lecture of the Pharmaceutical Society of Japan", p. 233 (1978).
Miyano et al., "Synthesis", p. 701 (1978).
Miyano et al., "J. Heterocyclic Chem.", vol. 19, p. 1465 (1982).

*Primary Examiner*—David B. Springer
*Attorney, Agent, or Firm*—Armstrong, Nikaido, Marmelstein, Kubovcik & Murray

[57] ABSTRACT

7a-Nitromethyl-2,3,5,6,7,7a-hexahydro-1H-pyrrolizine of the formula

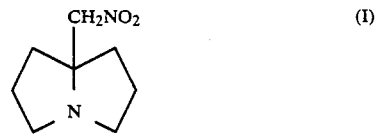

and salts thereof, as well as processes for the preparation of the compound and 7a-aminomethyl-2,3,5,6,7,7a-hexahydro-1H-pyrrolizine and salts thereof.

2 Claims, No Drawings

PYRROLIZINE DERIVATIVE AND ITS MANUFACTURE

BACKGROUND OF THE INVENTION

1. Field of the Invention

The present invention relates to a novel pyrrolizine derivative and a process for the preparation thereof, and more particularly to 7a-nitromethyl-2,3,5,6,7,7a-hexahydro-1H-pyrrolizine, process for the preparation thereof as well as process for the preparation of 7a-aminomethyl-2,3,5,6,7,7a-hexahydro-1H-pyrrolizine.

2. Related Arts 7a-aminomethyl-2,3,5,6,7,7a-hexahydro-1H-pyrrolizine of the following formula has been known as one of useful compounds for preparing various pharmaceutical and agricultural medicines, since it has an alkaroid skeletone therein.

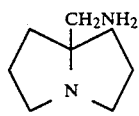
(III)

Further, the compound can also be employed as the raw material for synthesizing organo-platinum complexes [Jap. Pat. No. Sho 61-229893 (A)], 2-oxopyrrolidine compounds and salts thereof [Jap. Pat. No. Sho 61-254587 (A)] as well as cephalosporin derivatives [Jap. Pat. No. Sho 62-16487 (A)].

As far as the synthesis of 7a-aminomethyl-2,3,5,6,7,7a-hexahydro-1H-pyrrolizine is concerned, only one method has been known, wherein 7a-cyano-2,3,5,6,7,7a-hexahydro-1H-pyrrolizine is reduced with use of lithium aluminum hydride [Miyano et al. "Abstract on the 97th Annual Lecture of the Pharmaceutical Society of Japan", page 223 (1978)]. In this case, the raw material of 7a-cyano-2,3,5,6,7,7a-hexahydro-1H-pyrrolizine has been prepared by reacting γ-butyrolactone with KOCN, thermally treating the resulting γ-(N-2-pyrrolidinonyl)butyric acid in the presence of soda lime, reacting the resulting 2,3,5,6-tetrahydro-1H-pyrrolizine with perchloric acid, and reacting the resulting 1,2,3,5,6,7-hexahydropyrrolizinium perchlorate with potassium cyanide [Miyano et al. "Synthesis", page 701 (1978)]. Such a process has also been proposed for preparing said γ-(N-2-pyrrolidinonyl)butyric acid that γ-butyrolactone is added to a reaction mixture of 2-pyrrolidone and sodium [Miyano et al. "J. Heterocyclic Chem.", Vol. 19, page 1465 (1982)].

Further, it has been known as the process for the preparation of 7a-substituted-2,3,5,6,7,7a-hexahydro-1H-pyrrolizine derivatives that said 1,2,3,5,6,7-hexahydropyrrolizinium perchlorate is reacted with one of various nucleophilic reagents, or that the cyano group in said 7a-cyano-2,3,5,6,7,7a-hexahydro-1H-pyrrolizine is chemically modified or changed.

The following is summary of said related arts, shown by chemical formulae.

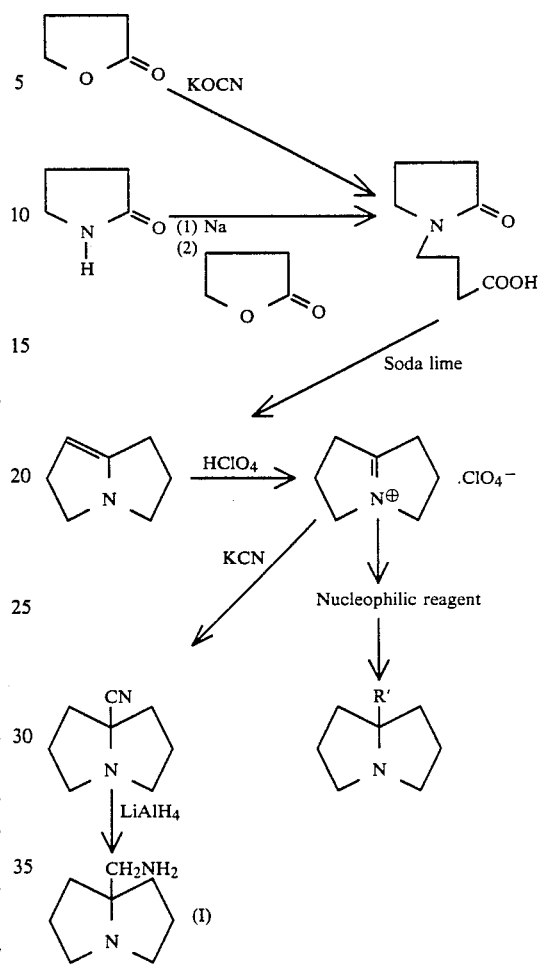

The conventional process for preparing 7a-aminomethyl-2,3,5,6,7,7a-hexahydro-1H-pyrrolizine as referred to, however, has disadvantages as stated below.

The first step of that γ-butyrolactone is reacted with KOCN to synthesize γ-(N-2-pyrrolidinonyl)butyric acid has problems in that a relatively high temperature (about 200° C.) is required for the reaction, and that yield of the product is somewhat low (about 40%). Such a process developed as another or separate method that after the reaction between 2-pyrrolidone and sodium, γ-butyrolactone is added to synthesize γ-(N-2-pyrrolidinonyl)butyric acid has a problem in that there is possibility of causing an explosion or the like abnormal reaction.

The second step of that γ-(N-2-pyrrolidinonyl)butyric acid is thermally treated in the presence of soda lime to synthesize 2,3,5,6-tetrahydro-1H-pyrrolizine has problems in that a relatively high temperature (about 250°–300° C.) is required for the reaction, and that the resulting compound has a relatively low stability.

Further, the final step of that 7a-cyano-2,3,5,6-tetrahydro-1H-pyrrolizine is reduced to synthesize 7a-aminomethyl-2,3,5,6,7,7a-hexahydro-1H-pyrrolizine has also problems of that an expensive lithium almínum hydride is required as the reduction reagent, and that the reaction should be carried out in an anhydrous solvent.

Each of the processes, wherein 1,2,3,5,6,7-hexahydropyrrolizinium perchlorate is reacted with the nucleophilic reagent, or cyano group in 7a-cyano-2,3,5,6,7,7a-hexahydro-1H-pyrrolizine is chemically modified has the disadvantage of that a production of its starting material is difficult, as referred to.

SUMMARY OF THE INVENTION

An essential target of the invention lies, therefore, in establishment of a process for preparing the pharmacologically useful compound of 7a-aminomethyl-2,3,5,6,7,7a-hexahydro-1H-pyrrolizine and salts thereof, which is easy in synthetic operation, ensures a high safety in work, requires no expensive reagent, and is suitable for an industrial scale production thereof.

A final object of the invention is, therefore, to provide a novel process for preparing 7a-aminomethyl-2,3,5,6,7,7a-hexahydro-1H-pyrrolizine.

Basic objects of the invention are to provide a novel compound as a convenient intermediate for preparing said final compound, as well as a process for preparing the intermediate.

According to the invention, one of the basic object can be attained by that said intermediate is 7a-nitromethyl-2,3,5,6,7,7a-hexahydro-1H-pyrrolizine of the formula

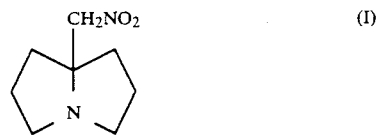

or a salt thereof.

As the salts of said compound (I), followings can exemplarily be listed. Hydrochloride, hydrobromide, hydroiodide, perchlorate or the like hydrohalogenate; sulfate, nitrate, phosphorate or the like mineral acid salt; acetate, propionate, glycolate, maleate, fumalate, tartrate, succinate, lactate, benzoate, cinnamate or the like organic carboxylate; methanesulfonate or the like alkanesulfonate; benzenesulfonate, p-toluene sulfonate or the like aryl sulfonate; cyclohexanesulfonate or the like cycloalkanesulfonate.

The compound (I) and salts thereof are novel one not reported in any literature, and according to the invention, can be prepared by reacting 1,7-di-substituted-4-heptanone of the formula

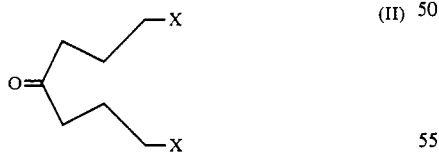

wherein X is a halogen atom or group of R-SO₃, in which R is a hydrocarbon group, with nitromethane and ammonia, and if necessary, converting the resulting compound into the salt. In this case, the raw material of 1,7-di-substituted-4-heptanone can easily be synthesized by starting from easily available material of γ-butyrolactone and in accordance with the method disclosed by H. Hart in "J. Am. Chem. Soc.", Vol. 78, page 112 (1956).

In the compound (II), the halogen atom may be of chlorine atom, bromine atom or iodine atom. The hydrocarbon group for the symbol R is one selected from alkyl and aryl groups, in which as the alkyl group, methyl, ethyl, n-propyl, n-butyl, n-pentyl, n-hexyl, n-decyl or the like straight chain alkyl group having 1 to 10 carbon atoms; i-propyl, i-butyl, sec-butyl, tert-butyl, i-pentyl or the like branched chain alkyl radical; cyclopropyl, cyclobutyl, cyclopentyl, cyclohexyl, cycloheptyl or the like cycloalkyl group having 3 or more carbon atoms may exemplarily be listed: and as the aryl group, phenyl, tolyl, xylyl, mesityl or the like may exemplarily be listed.

The synthetic reaction for the compound (I) will be completed for 12–48 hours, when 1 to 10 equivalent amount of nitromethane and 3 to 10 equivalent amount of ammonia were added, based on 1 equivalent amount of the compound (II), to stir the mixture at a temperature ranging from 20° to 50° C., in the presence or absence of a solvent. The resulting reaction mixture is made basic by adding thereto an alkali solution, and extracted with an organic solvent. After concentration of the extract, the resulting residue was distilled in vacuo to separate the desired 7a-nitromethyl-2,3,5,6,7,7a-hexahydro-1H-pyrrolizine. A salt thereof can be obtained by reacting the compound with an acid, in accordance with a manner known per se.

An addition of ammonia in the reaction system may be carried out in any manner. Namely, the ammonia in total required amount may be dissolved in a solvent to feed same in the reaction system, ammonia gas may be blown into the reaction system, with a time interval, so as to maintain its amount in the level of 0.5 to 3 equivalent amount, the reaction may be carried out in ammonia atmosphere, or any combination thereof may be employed. As the solvent, methanol, ethanol, n-propanol, i-propanol or the like alcohol; N,N-dimethylformamide, ethyl ether, tetrahydrofuran, dioxane or the like ether may exemplarily be listed. As the alkali for making the reaction mixture basic, sodium hydrate, potassium hydrate, sodium carbonate, potassium carbonate or the like may be listed. As the extraction solvent, methylene chloride, chloroform, ethyl ether, ethyl acetate or the like may be listed.

According to the process of the invention, further, 7a-aminomethyl-2,3,5,6,7,7a-hexahydro-1H-pyrrolizine of the formula

or a salt thereof can be prepared by reducing said compound (I) or salt thereof, and if necessary, converting the resulting compound into the salt, so that the final object as referred before can be attained.

The salts of the compound (III) are those as stated before on the compound (I). The reduction of the compound (I) can be carried out by treating same with an acid in the presence of a metal or a metal salt, or by hydrogenating the same in the presence of a metal catalyst. As the metal for the reducing reaction, iron, zinc, tin or the like may be listed. As the metal salt, stannous chloride, ferrous chloride or the like may be listed. As the acid, hydrochloric acid, hydrobromic acid, hydroiodic acid, perchloric acid or the like hydrohalogenic acid; surfuric acid, nitric acid, phosphoric acid or the like mineral acid; acetic acid, propionic acid, benzoic acid or the like organocarboxylic acid; methanesulfonic acid or the like alkanesulfonic acid; p-toluenesulfonic acid or the like arylsulfonic acid; cyclohexanesulfonic acid or the like cycloalkanesulfonic acid may be listed. As the metallic catalyst, Raney nickel, platinum oxide, palladium carbon or the like may be listed.

Among two types of said reducing reaction, the former type reaction will be completed within 0.5 to 6 hours, when 1 equivalent amount of 7a-nitromethyl-2,3,5,6,7,7a-hexahydro-1H-pyrrolizine or a salt thereof and 3 to 10 equivalent amount of the acid and 3 to 10 equivalent amount of the metal or the metal salt were dissolved in a suitable solvent to stir the mixture at room temperature. As the solvent, methanol, ethanol, n-propanol, i-propanol or the like alcohol; water; or a mixture of water and an alcohol may be listed. After completion of the reaction, insoluble matters were filtered off, the filtrate was, if necessary, concentrated in vacuo, adding thereto an alkali solution, filtering off, if necessary, insoluble matters, distilling out the solvent, extracting with use of an organic solvent, concentrating the extract, and distilling the residue; or after completion of the reaction, an alkali carbonate or a solution thereof was added to the reaction mixture, filtering off formed insoluble matters, concentrating the filtrate in vacuo, dissolving or suspending the resulting residue in an organic solvent, stirring same for 1 to 12 hours at 20° C., while introducing ammonia gas, filtering-off insoluble matters, concentrating the filtrate in vacuo, and then distilling in vacuo to afford the desired 7a-aminomethyl-2,3,5,6,7,7a-hexahydro-1H-pyrrolizine (Compound III). As the alkali for alkalidizing the reaction mixture, sodium hydroxide, potassium hydroxide, sodium carbonate, potassium carbonate, sodium hydrogen carbonate or the like may be listed. As the extraction solvent, methylene chloride, chloroform, ethyl ether, ethyl acetate or the like may be listed. While, as the basic carbonate, sodium carbonate, sodium hydrogen carbonate, potassium carbonate, potassium hydrogen carbonate, calcium carbonate or the like may be listed. As the organic solvent for dissolving or suspending the residue, benzene, toluene, tetrahydrofuran, dioxane or the like ether solvent; methanol, ethanol, i-propanol, n-propanol, i-butanol, n-butanol or the like alcoholic solvent may be listed.

Among two types of said reducing reaction, the latter type reaction will be completed within 0.5 to 12 hours, when 7a-nitromethyl-2,3,5,6,7,7a-hexahydro-1H-pyrrolizine or a salt thereof and the metal catalyst and if necessary, a basic compound were dissolved or suspended in a suitable solvent to stir the mixture at room temperature, under hydrogen atmosphere. As the basic compound, sodium hydroxide, potassium hydroxide, calcium hydroxide, sodium carbonate, potassium carbonate, calcium carbonate, sodium hyrogen carbonate or the like may be listed. As the solvent, methanol, ethanol, n-propanol, i-propanol or the like alcohol; acetic acid, propionic acid or the like organic acid, hydrochloric acid, surfuric acid, nitric acid, perchloric acid or the like mineral acid solution; water; a mixture thereof may be listed. After completion of the reaction, insoluble matters were filtered off, the filtrate was concentrated in vacuo, and then distilled in vacuo, or after the filtration, the filtrate was, if necessary, concentrated in vacuo, making to basic with an alkali solution, extracting with an organic solvent, concentrating the extract, and then distilling the residue in vacuo, or after the filtration, the filtrate was added to an acid solution or to the filtrate was added the acidic solution, the resulting solution was, if necessary, concentrated in vacuo, the precipitated crystal was gathered, if necessary, recrystallized, suspended in an organic solvent, the suspension was stirred with introducing NH$_3$ at room temperature for 1 to 12 hours, insoluble matters were filtered off, concentrating the filtrate, and then distilling the residue in vacuo, to afford the desired 7a-aminomethyl-2,3,5,6,7,7a-hexahydro-1H-pyrrolizine (Compound III). As the alkali for making the reaction mixture basic, sodium hydroxide, potassium hydroxide, sodium carbonate, potassium carbonate, sodium hydrogen carbonate or the like may be listed. As the extraction solvent, methylene chloride, chloroform, ethyl ether, ethyl acetate or the like may be listed. As the acid solution, hydrogen chloride, hydrogen bromide, hydrogen iodide, sulfuric acid or the like in methanol, ethanol, i-propanol, ethyl ether, benzene, toluene, xylene or the like may be listed. As the recrystallizing solvent, ethanol, n-propanol, i-propanol, n-butanol, i-butanol or the like may be listed. As the solvent for making suspension, n-haxane, cyclohexane, n-pentane, benzene, toluene, xylene, ethyl ether, i-proppanol, n-butanol, i-butanol or the like may be listed.

DETAILED DESCRIPTION OF PREFERRED EMBODIMENTS

The invention will now be further explained in more detail with reference to Examples.

EXAMPLE 1

7a-Nitromethyl-2,3,5,6,7,7a-hexahydro-1H-pyrrolizine

To a solution of nitromethane (0.67 g, 11 mmol) in 0.3 ml of 16% NH$_3$/MeOH, 1,7-dichloro-4-heptanone (0.50 g, 2.7 mmol) was added dropwise at 20° C. The resulting solution was stirred for 24 hours at 20° C. under ammonia gas atmosphere. The reaction mixture was concentrated and 0.1N NaOH was added to the residue to extract with methylene chloride. The extract was dried over anhydrous sodium sulfate, concentrated and distilled in vacuo to afford 0.42 g of the desired compound (Yield: 90%).

Boiling point: 83°–84° C. (0.5 mmHg).

$^1$H-NMR spectrum (CDCl$_3$) δ ppm:

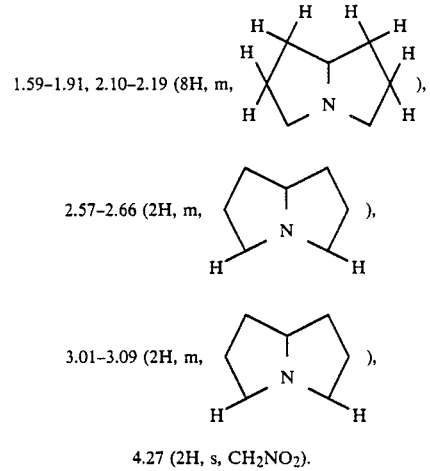

IR spectrum ($\nu_{max}^{neat}$) cm$^{-1}$: 2958, 2870, 2818 (C—H), 1547 (NO$_2$), 1100 (C—N).

MS spectrum (EI/DI) m/z: 170 (M+), 110 (base peak).

MS spectrum [CI/DI (i-Bu)] m/z: 171 [(M+1)+], 110 (base peak).

High resolution MS spectrum (m/z): 170.2135 (M+, $C_8H_{14}N_2O_2$, Calcd. 170.2130).

EXAMPLE 2

7a-Nitromethyl-2,3,5,6,7,7a-hexahydro-1H-pyrrolizine hydrochloride

To a solution of 7a-nitromethyl-2,3,5,6,7,7a-hexahydro-1H-pyrrolizine (170 mg, 1.00 mmol, obtained in Example 1) in 0.50 ml of methylene chloride, 20% HCl/MeOH (0.50 ml) was added at 20° C., the resulting reaction mixture was concentrated in vacuo, and then ethyl acetate was added to the residue to cause crystallization. The crystals were obtained by filtration and recrystallized from chloroform to afford 165 mg of the desired hydrochloride (Yield: 80%).

Melting point: 125°–128° C.

Elementary analysis ($C_8H_{15}ClN_2O_2$): Cal.: C 46.49, H 7.31, N 13.55, Found: C 46.51, H 7.25, N 13.60.

EXAMPLE 3

7a-Aminomethyl-2,3,5,6,7,7a-hexahydro-1H-pyrrolizine

To 5.0 ml of 80% ethanol, 7a-nitromethyl-2,3,5,6,7,7a-hexahydro-1H-pyrrolizine (300 mg, 1.76 mmol, obtained in Example 1) and concentrated hydrochloric acid (0.45 ml, 5.28 mmol) were added to stir for 10 minutes at 20° C. Then, iron powder (500 mg, 8.95 mmol) was added to the mixture to further stirr for 1 hour at 20° C. Insoluble matters were filtered off and the filtrate was concentrated, adding 0.5N NaOH (10 ml) to the residue, filtering the solution to further remove insoluble matters, extracting the filtrate with chloroform, drying the extract over anhydrous sodium sulfate, concentrating the extract, and distilling the resulting crude product to afford 224 mg of the desired compound (Yield: 91%).

Boiling point: 46°–49° C. (3 mmHg).

$^1$H NMR spectrum (CDCl$_3$) δ ppm:

1.40 (2H, br.s, NH$_2$), 1.49–1.83 (8H, m, 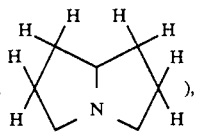 ), 2.53 (2H, s, C$\underline{H}_2$NH$_2$), 2.60–2.66 (2H, m, 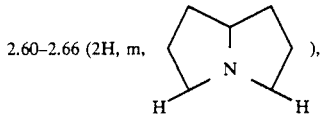 ), 2.93–3.02 (2H, m, 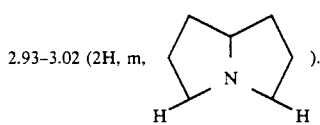 ).

IR spectrum ($\nu_{max}^{neat}$) cm$^{-1}$: 3380 (N—H), 2950 (C—H), 1460, 1100, 840.

MS spectrum (EI/DI) m/z: 110 (base peak).
MS spectrum [CI/DI (i-Bu)] m/z: 141 [(M+1)+].

EXAMPLE 4

7a-Aminomethyl-2,3,5,6,7,7a-hexahydro-1H-pyrrolizine

To a suspension of Raney nickel (300 mg) in 5.0 ml of ethanol, 7a-nitromethyl-2,3,5,6,7,7a-hexahydro-1H-pyrrolizine (300 mg, 1.76 mmol, obtained in Example 1) was added and the resulting mixture was stirred for 1 hour at 20° C. under hydrogen atmosphere. The catalyst was filtered off, the filtrate was concentrated, and the resulting crude product was distilled in vacuo to afford 185 mg of the desired compound (Yield: 75%).

Physical data of the compound were same with those in Example 3.

EXAMPLE 5

7a-Aminomethyl-2,3,5,6,7,7a-hexahydro-1H-pyrrolizine

To a solvent mixture of i-propanol (20 ml) and water (5 ml), 7a-nitromethyl-2,3,5,6,7,7a-hexahydro-1H-pyrrolizine (1.28 g, 7.53 mmol), obtained in Example 1) and concentrated hydrochloric acid (1.91 ml, 22.6 mmol) were added and the mixture was stirred for 10 minutes at 20° C. Then, iron powder (1.04 g, 18.1 mmol) was added to the mixture to further stirr for 4 hours at 20° C. While stirring the reaction mixture, sodium hydrogen carbonate was added at a temperature lower than 20° C., to make the same into a suspension having pH of 8 to 9. The suspension was filtered to remove insoluble matters, concentrating the filtrate in vacuo, suspending the resulting residue in i-propanol (6.0 ml), and introducing ammonia gas therein to stir the suspension for 12 hours at 20° C. After filtering off insoluble matters, the filtrate was concentrated in vacuo and the resulting crude product was distilled in vacuo to afford 840 mg of the desired compound (Yield: 80.0%).

Physical data of the compound were same with those in Example 3.

EXAMPLE 6

7a-Aminomethyl-2,3,5,6,7,7a-hexahydro-1H-pyrrolizine

To a homogenous solution of 7a-nitromethyl-2,3,5,6,7,7a-hexahydro-1H-pyrrolizine (1.00 g, 5.88 mmol) and NaOH (0.235 g (5.88 mmol) in 5 ml of ethanol, 0.40 g of Raney nickel were added to stir the mixture under hydrogen atmosphere at 20° C. for 12 hours. The catalyst was filtered off, and then the filtrate was poured into 33% HCl/ipropanol (5.0 ml) below 20° C. The reaction mixture was evaporated to dryness to give crude crystal. The crude crystal was suspended in toluene (5.0 ml) and to the suspension was introduced NH$_3$ gas to stir at 20° C. for 12 hours. The precipitate was filtered off and the filtrate was evaporated to afford 716 mg of the desired compound (Yield: 86.9%).

Physical data of the compound were same with those in Example 3.

What is claimed is:

1. 7a-Nitromethyl-2,3,5,6,7,7a-hexahydro-1H-pyrrolizine of the formula

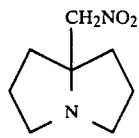
(I)
and a salt thereof.
2. A process for the preparation of 7a-nitromethyl-2,3,5,6,7,7a-hexahydro-1H-pyrrolizine of the formula
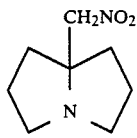
(I)
and a salt thereof, which comprises a step of reacting 1,7-disubstituted-4-heptanone of the formula
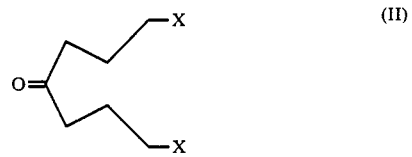
(II)
wherein X is a halogen atom or group of R-SO₃, in which R is a hydrocarbon group,
with nitromethane and ammonia, and if necessary, converting into the salt.
* * * * *